United States Patent [19]

Seidenberger

[11] 4,226,600

[45] Oct. 7, 1980

[54] MERCURY CONTAMINATION INDICATOR AND DECONTAMINATION AID

[75] Inventor: James W. Seidenberger, Royersford, Pa.

[73] Assignee: J. T. Baker Chemical Company, Phillipsburg, N.J.

[21] Appl. No.: 969,020

[22] Filed: Dec. 13, 1978

[51] Int. Cl.³ .................. G01N 21/78; G01N 31/22
[52] U.S. Cl. ...................... 23/232 R; 23/230 R; 252/408
[58] Field of Search .............. 23/232 R, 230 R; 252/408

[56] References Cited

U.S. PATENT DOCUMENTS

| | | | |
|---|---|---|---|
| 2,567,251 | 9/1951 | Stitt | 23/232 R |
| 3,826,618 | 7/1974 | Capuano | 23/232 R |
| 3,933,431 | 1/1976 | Trujillo | 23/232 R |

OTHER PUBLICATIONS

A. F. Scott et al., Chemistry, 48(5), 29–30, (May 1975).
E. Browning, "Toxicity of Industrial Metals", 207–208, Butterworths, London, 1961.

*Primary Examiner*—Sidney Marantz
*Attorney, Agent, or Firm*—George W. Rauchfuss, Jr.; Eugene O. Retter

[57] ABSTRACT

A composition for detection of the presence of mercury or mercury vapor comprises a formulation of cuprous iodide or silver iodide in combination with powdered elemental sulfur.

6 Claims, No Drawings

MERCURY CONTAMINATION INDICATOR AND DECONTAMINATION AID

FIELD OF THE INVENTION

This invention relates to a composition for indicating the presence of mercury and for use in complexing small amounts of mercury as a decontamination aid.

BACKGROUND OF THE INVENTION

In recent years, it has been determined that spilled liquid mercury can produce a substantial health hazard by contaminating the surrounding ambient atmosphere with mercury vapor which volatilizes from the spilled liquid mercury. Moreover collecting all the spilled mercury in any particular spill is extremely difficult because of the high surface tension and high density of liquid elemental mercury. It has, however, recently been recognized that relatively small amounts of liquid mercury which can escape collection can result in a mercury vapor level above the safe limits for such mercury contamination. Moreover, such small amounts of mercury which are not collected are susceptible of escaping detection and thus, the amount of mercury will not be reduced to a level sufficient to bring the mercury vapor contamination below the safe level. Thus, it is highly desirable to be able to detect the presence of mercury and mercury vapor in an area in order to reduce the mercury vapor contamination to an absolute minimum since the effects of mercury on the human body are cumulative and thus, prolonged exposure to even minute amounts of mercury vapor or other mercury contamination can result in accumulating sufficient amounts to bridge the safe or toxic levels.

PRIOR ART

The use of cuprous iodide in the dry state to react with mercury or mercury vapor to form a colored cuprous mercuric iodide complex and thereby provide a means of detecting mercury vapors is generally known. Moreover, the use of filter paper impregnated with cuprous iodide as a color method for the detection of mercury vapor has been reported at pages 29 and 30 of the May 1975 issue of Chemistry. Additionally, it has been recognized that cuprous iodide precipitate can be used as a means to detect small quantities of mercurous or mercuric ion in solution. Cuprous iodide in the dry state will react with mercury or mercury vapor and the cuprous mercuric iodide complex formed is scarlet colored and when formed on the surface of exposed cuprous iodide imparts a pink or salmon color to the buff or cream colored cuprous iodide thereby indicating the presence of mercury or mercury vapor.

SUMMARY OF THE INVENTION

It has been discovered that a greatly improved composition for detection of the presence of mercury or mercury vapor comprises a dry powder formulation of cuprous iodide or silver iodide in combination with powdered elemental sulfur.

DETAILS OF THE INVENTION

Dry powder formulations of from about 5 to about 95% by weight of either cuprous iodide or silver iodide with about 95 to 5% by weight of powdered elemental sulfur are useful compositions according to this invention. A preferred composition comprises a 1:1 mixture of the iodide with the sulfur. Such compositions yield a complexing color reaction that is more highly distinctive than that obtained with the complexing reaction of the metal halide alone with mercury or mercury vapor. Reaction of mercury or mercury vapor with the mixtures of this invention yields black or dark brown colored products. These products present a much more visible contrast against the buff or cream color of the unreacted metal halides/sulfur mixture background than does the pink or salmon colored metal mercuric iodide complexes of the metal iodides alone with mercury or mercury vapor. This more highly visible contrast permits more sensitivity in visual detection and more positive and easier identification of the presence of mercury or mercury vapor. The identity of the reaction products obtained when mercury or mercury vapor is permitted to react with the compositions of this invention has not been determined. It is believed that the dark color may be contributed by the formation of the respective metallic sulfides catalyzed in some manner by the formation of the metallic mercuric iodide complexes in the presence of the elemental sulfur.

Additionally, it has been found that the migration rate of the dark colored reaction outward from a mercury source embedded in or covered by the metallic iodide/sulfur mixture of this invention is about half that of the rate in pure metallic halide. This indicates that such a composition is less prone to penetration by mercury vapor than a pure metallic iodide. The faster penetration of mercury vapors through and out over the surface of a covering layer of the pure metallic iodide indicator tends to cause a more homogeneous darkening of the indicator surface as a whole. This effect lessens the color contrast seen in the immediate area of the mercury thereby reduces the indicator's sensitivity and capacity to accurately locate specific areas of microscopic mercury contamination. Thus, the slower yet acceptable penetration rate of the mercury vapors through the indicator mixtures of this invention permits more sensitive and accurate location of mercury contamination.

Although the indicator mixtures of this invention can be employed as the powder mixtures per se such as in applying thin layers of said powder to a horizontal surface suspected of mercury contamination, the powders can also be formed into slurries, with water or any other suitable inert vehicle, and painted or coated onto vertical surfaces suspected of mercury contamination. Likewise, the powder mixtures can, for example, be coated onto or combined with inert substrates and utilized in that form such as for example, combined with activated carbon, silica gel, granulated carbon, starch or the like.

It will also be recognized that the compositions may be used in areas of light or relatively minimal mercury contamination to decontaminate the area by reaction with the mercury.

To illustrate the operability of the composition of this invention, filter paper discs were contaminated with microdrops of mercury metal at a level of about 0.29 mgHg/cm$^2$. The left side of the paper was covered with 1.0 g of cuprous iodide/sulfur 1:1 mixture and the right side of the disc with 1.0 g cuprous iodide alone. Photographs were taken immediately after application and at times of 1, 2, 3, 4 and 21 hours afterward. Visual inspection of the comparative test demonstrates the superior sensitivity and color visualization capacity of the cuprous iodide/sulfur mixture for locating microscopic mercury contamination.

I claim:

1. A composition of matter comprising a mixture of about 5 to 95% by weight of a metal iodide selected from the group consisting of cuprous iodide and silver iodide in combination with about 95 to 5% by weight of elemental sulfur.

2. A method for detecting the presence or absence of mercury or mercury vapor in an area of suspected mercury contamination comprising exposing the area to the composition of claim 1.

3. The composition of claim 1 comprising a mixture of the iodide with the sulfur in a weight ratio of about 1 to 1.

4. The composition of claim 3 wherein the iodide is cuprous iodide.

5. The composition of claim 3 wherein the iodide is silver iodide.

6. A method detecting the presence or absence of mercury or mercury vapor in an area of suspected mercury contamination comprising exposing the area to the composition of claim 3.

* * * * *